(12) United States Patent
Miceli et al.

(10) Patent No.: US 6,369,799 B1
(45) Date of Patent: Apr. 9, 2002

(54) COMPUTER POINTER DEVICE FOR HANDICAPPED PERSONS

(75) Inventors: Frank Miceli; John Albert Maze; William Graham Easter, all of Orlando, FL (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/360,134

(22) Filed: Jul. 23, 1999

(51) Int. Cl.[7] .......................... G09G 5/08; H03K 17/94; H03M 11/00; H04Q 1/00
(52) U.S. Cl. ...................... 345/167; 345/156; 345/163; 341/20; 341/21; 340/825.19
(58) Field of Search ................................ 345/156, 157, 345/163, 164, 167, 168, 169, 161; 341/20, 21; 340/825.19

(56) References Cited

U.S. PATENT DOCUMENTS

| | | | |
|---|---|---|---|
| 3,854,131 A | 12/1974 | Vanderheiden et al. | 340/365 L |
| 4,862,165 A | 8/1989 | Gart | 341/20 |
| 5,157,381 A | 10/1992 | Cheng | 340/710 |
| 5,186,629 A | 2/1993 | Rohen | 434/114 |
| 5,287,102 A | 2/1994 | McKiel, Jr. | 340/825.19 |
| 5,305,017 A | 4/1994 | Gerpheide | 345/174 |
| 5,311,210 A * | 5/1994 | O'Brien et al. | 345/168 |
| 5,334,997 A * | 8/1994 | Scallon | 345/167 |
| 5,340,067 A | 8/1994 | Martin et al. | 248/118.5 |
| 5,355,147 A | 10/1994 | Lear | 345/156 |
| 5,726,683 A | 3/1998 | Goldstein et al. | 345/168 |
| 5,745,055 A * | 4/1998 | Rdlich et al. | 341/20 |
| 5,764,164 A * | 6/1998 | Cartabiano et al. | 341/20 |
| 5,805,142 A | 9/1998 | Byrne | 345/163 |
| 5,833,180 A | 11/1998 | Baranowski | 248/118 |
| 5,889,510 A * | 3/1999 | Klarlund | 345/168 |
| 6,091,402 A * | 7/2000 | Howell | 345/157 |

FOREIGN PATENT DOCUMENTS

| | | |
|---|---|---|
| EP | 0831419 A1 | 3/1998 |
| JP | 08095703 | 4/1996 |
| JP | 09054655 | 2/1997 |
| JP | 10020980 | 1/1998 |
| JP | 10063413 | 3/1998 |
| JP | 10143304 | 5/1998 |

OTHER PUBLICATIONS

Computer Search Results—Problem Solving Report, Question No. 1015274.024.
Computer Search Results—Problems Solving Report, Question No. 1015274.026.
Computer Search Results—Problem Solving Report, Question No. 1015274.027.

* cited by examiner

*Primary Examiner*—Bipin Shalwala
*Assistant Examiner*—David L. Lewis
(74) *Attorney, Agent, or Firm*—Synnestvedt & Lechner LLP

(57) ABSTRACT

A method and apparatus for controlling a pointer on a computer screen adapted for use by individuals with limited or no manual dexterity. A track ball is positioned to protrude from the upper surface of a generally partially cylindrically shaped base. A mating cradle sits on top of the base with its lower surface in contact with the upper surface of the track ball and the upper surface of the base. The upper surface of the cradle support is shaped to accept the forearm of an operator. The track ball is coupled in a known fashion to operate a pointer on a computer display. The operator can move the cursor up and down on the screen by pushing his or her arm outwardly or inwardly and can move the cursor left to right on the screen by rotating his or her arm in the cradle about its longitudinal axis.

14 Claims, 3 Drawing Sheets

COMPUTER POINTER DEVICE FOR HANDICAPPED PERSONS

FIELD OF INVENTION

The invention pertains to computer pointer control devices. More particularly, the invention pertains to computer pointer control devices adapted for ease of use by handicapped individuals.

BACKGROUND OF THE INVENTION

The use of pointers on graphical user interfaces (GUIs) presented on a computer display device for interacting with application software is well known. Essentially all Windows™ based or MacIntosh™ based software utilizes such control. Accordingly, apparatus for moving the pointer on a computer screen also are well known to computer operators. Probably the most common pointer control device is a computer mouse such as illustrated in FIG. 1. A computer mouse 10 comprises a shell 12 shaped to fit conveniently and comfortably in the palm of the hand of the user while it rests on a horizontal surface. It typically has two or more buttons 16 and 18 on its top surface positioned to be adjacent the operator's index and middle fingers when the mouse is gripped comfortably. Protruding from the bottom of the shell is a track ball (not shown) which, responsive to the user moving the mouse on top of the horizontal supporting surface, rotates due to friction with that surface. The track ball is coupled to circuitry (not shown) encased within the shell 12 which determines the direction and amount of rotation of the trackball and converts that to an electrical signal that is provided to the computer via a cable 19 that extends from the back of the mouse and is coupled to a mouse port on the computer. Software within the computer takes that information and converts it into corresponding movements of the pointer on the computer display device.

Although computer mouses of the general form shown in FIG. 1 are probably the most common type of pointer control device, many other types of computer pointer control devices are known. This is particularly true in connection with portable computers (e.g., laptop computers and palmtop computers) since computer mouses tend to be too cumbersome for laptop use. Well known computer pointer control devices other than a mouse include track balls, touch pads, and touch pens. A track ball is very similar to a mouse except that the track ball protrudes upwardly from a surface and the user rotates the track ball by directly placing his or her hand on the track ball and rotating it manually.

Light pens are used in conjunction with touch sensitive screens. A light pen comprises a pen-shaped object which is convenient to hold in the same manner as a pen but having an electrically conductive tip rather than an ink tip. When the light pen touches the electrically sensitive screen, the computer detects the location on the screen where the touch pen contacts the screen.

A touch pad comprises a plurality of layers of material, the top layer simply being a flat surface which can be touched without causing damage. Underneath the top layer are a plurality of rows and columns of electrodes separated by thin layers of insulation to form a grid of electrodes. Beneath the layers of electrodes is a printed circuit board to which the electrodes are coupled. The electrodes receive an alternating current which is interrupted when a conductive object, such as a finger, comes in close proximity to an electrode. In order to operate a touch pad, a user puts his or her finger on the touch pad and moves it about. The electrodes at which interruptions in current occur are detected by the circuit board and and transmitted to the computer. The computer translates that information in order to move a cursor on a computer screen in a manner corresponding to the movement of the user's finger.

U.S. Pat. No. 5,305,017 discloses one type of touch pad apparatus in common usage. It also contains brief descriptions (with references to more detailed descriptions) of many other types of computer pointer devices, including all of those discussed above and is incorporated herein by reference.

It is noteworthy that all of the most common computer pointer control apparatus require essentially full manual dexterity of the user. To date, little effort has been expended towards creating a computer pointer control device for persons with limited or no manual dexterity.

SUMMARY OF THE INVENTION

The invention is a method and apparatus for controlling a pointer on a computer screen adapted for use by individuals with limited or no manual dexterity. A track ball is positioned to protrude from the upper surface of a partially cylindrical base. A mating cradle sits on top of the base with its lower surface in contact with the upper surface of the track ball and the upper surface of the base. The upper surface of the cradle support is shaped to accept the forearm of an operator. The track ball is coupled in a known fashion to circuitry to operate a pointer on a computer screen. The operator can move the cursor up and down on the screen by pushing his or her arm outwardly or inwardly and can move the cursor left to right on the screen by rotating his or her arm in the cradle about its longitudinal axis.

In alternative embodiments, the track ball may be replaced with a touch pad and the bottom surface of the cradle may include a conductive protuberance while the remainder of the bottom surface is non-conductive so as to provide a small contact point between the cradle and the touch pad.

DETAILED DESCRIPTION OF THE INVENTION

Figure 1:
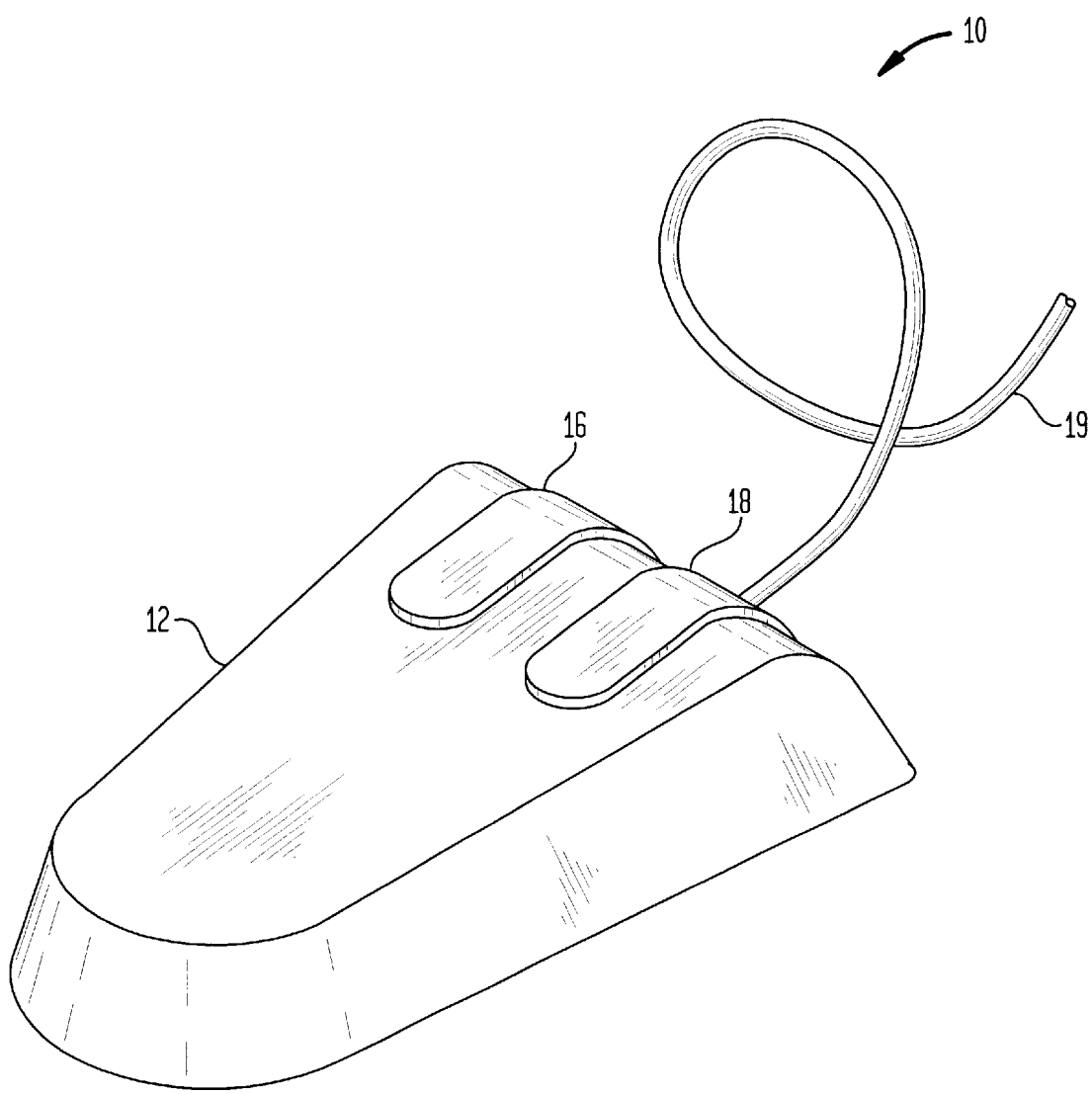
FIG. 1 is a perspective view of a computer mouse of the prior art.
Figure 2:
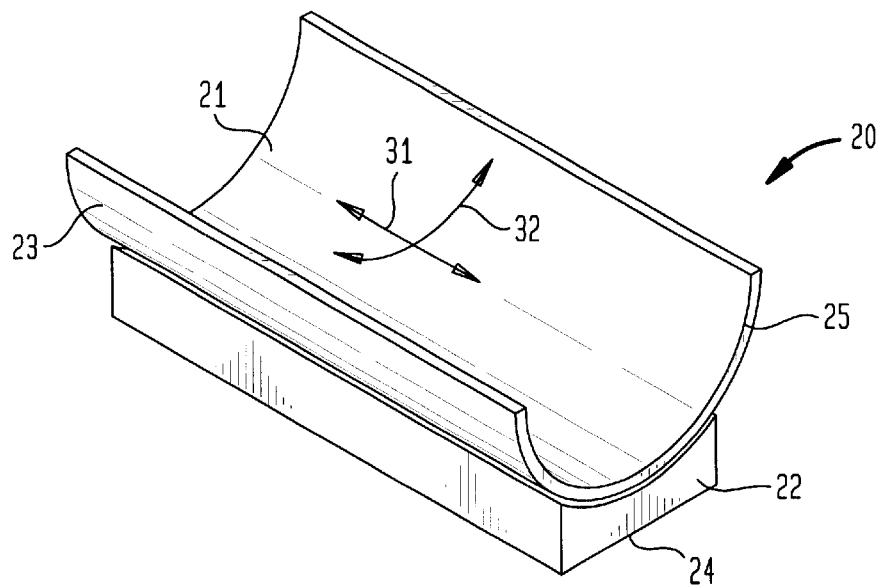
FIG. 2 is a perspective view of a computer pointer control device in accordance with a first embodiment of the present invention.
Figure 3:
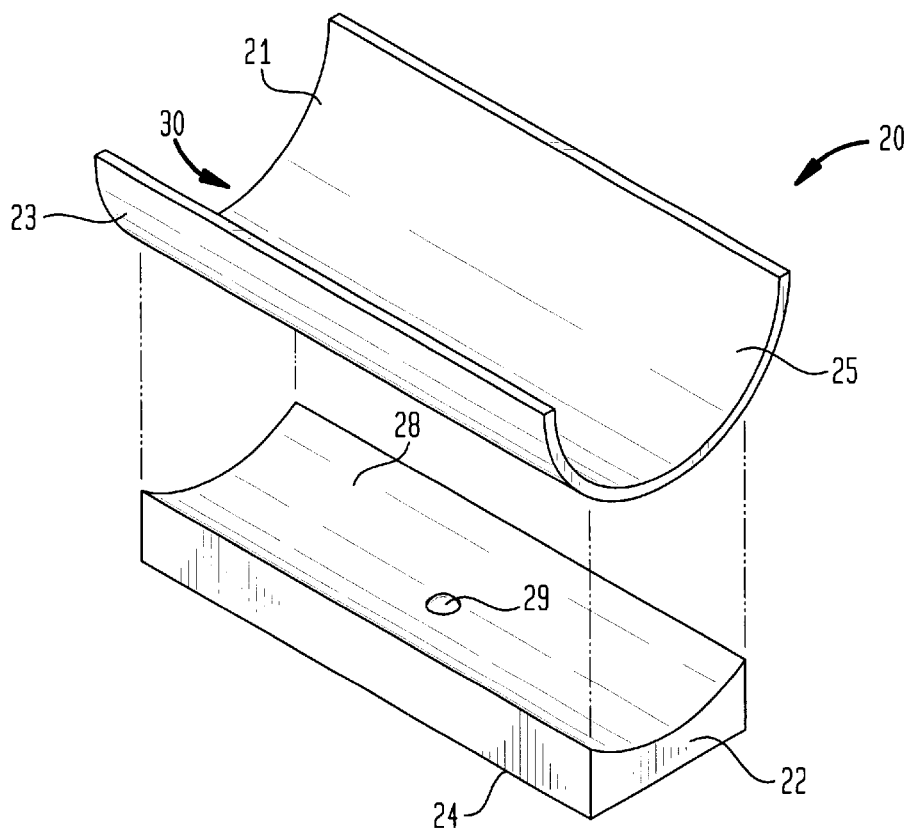
FIG. 3 is a blown-up view of the computer pointer control device of FIG. 2.
Figure 4:
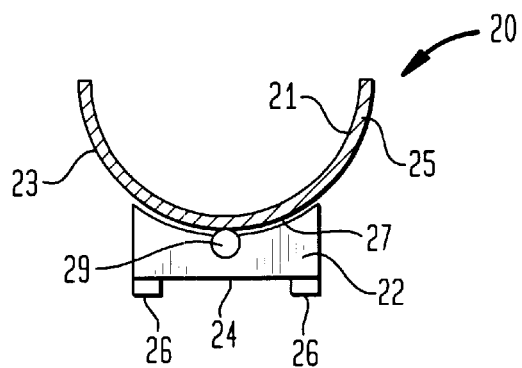
FIG. 4 is a cross sectional view of the computer pointer control device of FIG. 2.

FIGS. 2, 3 and 4 show a computer pointer control device 10 in accordance with a first embodiment of the present invention. A cradle support or base portion 22 is designed to rest on a support surface such as a table. Accordingly, its bottom surface 24 is generally flat and may have felt, rubber or plastic pads 26 at its corners in order to protect the surfaces of tables upon which it might rest. Its top surface 27 is generally semi-cylindrical in shape. Preferably, the top surface of the base forms between 10° and 180° of a complete arc of a cylinder. Most preferably the arc is within the range of about 30° to 120°. Embedded within the base 22 and protruding from the center of the top surface 27 of the base is a track ball 29. Within the base is the apparatus and circuitry associated with a track ball for holding it in place and creating an electrical signal representative of the direction and amount of rotation of the trackball and which is used by the computer to control the pointer on the screen. Such circuitry and apparatus are well-known in the art and do not form a part of the present invention. Accordingly, the details of such apparatus and circuitry will not be discussed further herein.

The device further comprises a cradle 25 having a bottom surface 23 designed to mate with the top surface 27 of the base 22. Accordingly, it is of semi-cylindrical shape also and is sized to mate with the top surface of the base. Preferably, the bottom surface 23 of the cradle 25 is either formed of or covered with a high friction, soft, material such that movement of the cradle on the base will cause the track ball to rotate through friction without damaging the track ball 29, the top surface 27 of the base or the bottom surface 23 of the cradle. For instance, a foamed rubber material such a neoprene (from which mouse pads are commonly formed) is one such material. The top surface 21 of the cradle 25 is also generally cylindrical. However, in a preferred embodiment, it is somewhat conical in shape and adapted to mate comfortably with a typical human forearm. Accordingly, it should taper towards the forward end 30.

In one embodiment, the cradle 25 is not fixed to the base 22, but rests freely and removably on top of the base. In other embodiments, the bottom surface of the cradle and the top surface of the base may have mating structures to lock the two together, yet allow for the cradle to move in two generally orthogonal directions as illustrated by arrows 20 and 22 in FIG. 2.

Preferably, the top surface 21 of the cradle 25 is formed of a material which is comfortable to remain in prolonged contact with human skin. A resilient foamed rubber, such as neoprene or a clothing type fabric are suitable. In fact, the cradle 25 may be entirely formed of such a material with a rigid plastic or metal form embedded in the middle of it in order to hold it in the desired, partially-cylindrical, shape.

In operation, a user with limited manual dexterity or no hand at all may place a forearm within the top surface 21 of the cradle. The operator can manipulate the track ball 29 in two generally orthogonal directions (or any combination thereof) as follows. Pushing one's arm forward (away from the body) or backwards (towards the body) will cause the track ball to rotate in a first direction (see arrow 31). Rotating one's forearm so as to rotate the cradle in the direction of arrow 32 will cause the track ball 29 to rotate in a orthogonal direction orthogonal to the first direction. Signals generated by the track ball are transmitted to the computer in the normal fashion to control the pointer on a computer display device.

Buttons can be provided separately for selecting items once the pointer has been positioned in the desired position on the computer display device. For instance, foot pedals or buttons for the user's other hand/limb can be provided.

Figure 5:
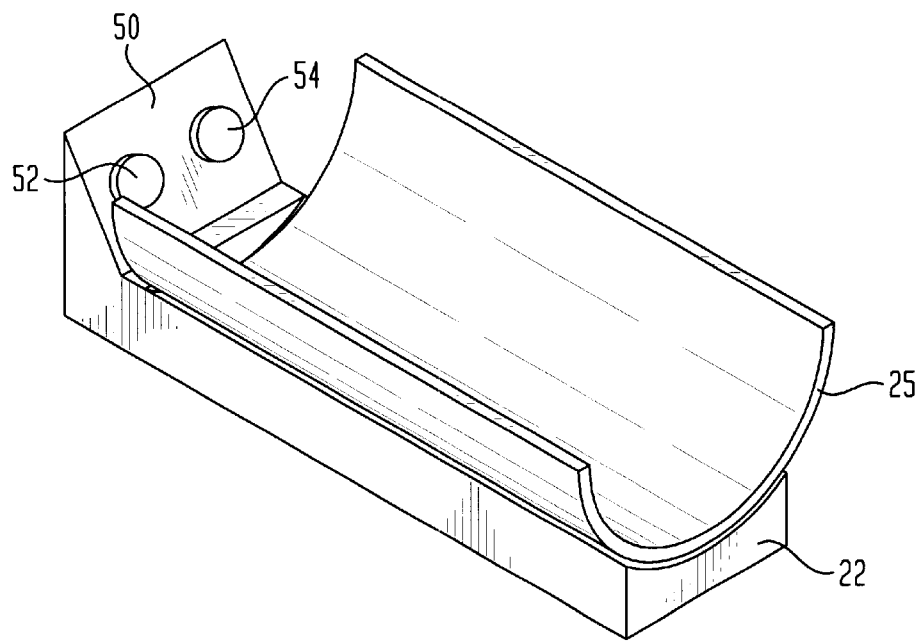
FIG. 5 is a perspective view of a computer control device in accordance with a second embodiment of the present invention.

However, FIG. 5 illustrates a second embodiment of the invention in which buttons usable by individuals with limited or no manual dexterity are included with the apparatus of the present invention. As shown in FIG. 5, the base may include an extension 50 for supporting a surface having two large buttons 52 and 54 positioned in front of the operator's forearm. In order to press the buttons, the user simply needs to manipulate the cradle as described above to place the pointer in the desired location on the display and then lifts his or her arm up off of the cradle and thrust it forward in order to press one of the buttons 52 or 54.

Figure 6:
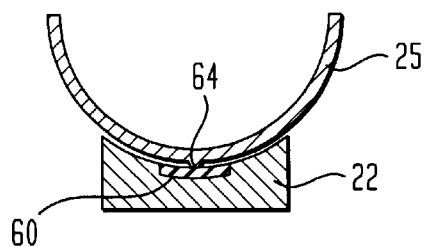
FIG. 6 is a cross-sectional view of a computer control device in accordance with a third embodiment of the present invention.

In another embodiment of the invention illustrated in FIG. 6, the track ball may be replaced by a touch pad 60. Preferably, the cradle is adapted to ensure that the material forming the bottom surface 62 of the cradle is not conductive. The cradle is further adapted to include a conductive protrusion 64 from its bottom surface. The contact of the protrusion 64 on the touch pad 60 provides a signal for controlling the computer pointer.

Accordingly, a person who has lost a hand or has limited manual dexterity may comfortably and effectively control a computer pointer.

Alternately, the cradle itself may be a touch pad and the users forearm itself can be used as the conductive object.

The invention can be adapted to various particular handicaps. For instance, persons unable to move their arms effectively would utilize a different embodiment of the invention. For instance, the invention can be adapted to be operable by foot. The computer pointer control device could be similar to any of the embodiments disclosed in FIGS. 2 through 6 except that the top surface of the cradle would be adapted to mate comfortably with the user's foot, rather than forearm. The bottom surface of the cradle and the top surface of the base may be semi-cylindrical, such as in FIGS. 2–5 so that left to right manipulation of the pointer is affected by rotation about one's ankle. However, even this can be changed. For instance, the top surface of the base and the bottom surface of the cradle may be flat so that left to right movement of the pointer is provided by left to right movement of the foot, rather than rotation of the foot about the ankle.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

I claim:

1. A computer pointer control device for persons with limited dexterity comprising:

a base having a top surface;

a translation device positioned in said top surface of said base;

a cradle having a front end, a back end, a bottom surface shaped to mate with said top surface of said base and contact said translation device, and a top surface adapted to accept a human limb;

said translation device adapted to detect movement of said cradle within said base;

a circuit for converting said detected movement into control signals for a computer device, whereby movement of said cradle is translated into control signals for said computing device; and an extension projecting upwardly from said base and in front of said front end of said cradle, said extension having at least one button positioned in front of said cradle, whereby an operator of said apparatus may operate said button with said limb;

wherein said top surface of said base and said bottom surface of said cradle are semicylindrical and mating whereby movement of said cradle along a longitudinal axis of said partially cylindrical top surface is converted into control signals corresponding to a first direction and rotation of said cradle about said longitudinal axis is converted into control signals corresponding to a second direction orthogonal to said first direction.

2. A computer pointer control device as set forth in claim 1 wherein said cradle is formed of rubber.

3. A computer pointer control device set forth in claim 1 wherein said cradle is formed of plastic.

4. A computer pointer control device as set forth in claim 2 wherein said cradle further comprises a rigid material shaped in a generally partially cylindrical form, said rigid material being wrapped in said rubber.

5. A computer pointer control device as set forth in claim 3 wherein said cradle further comprises a rigid material shaped in a generally partially cylindrical form, said rigid material being wrapped in said plastic.

6. A computer pointer control device as set forth in claim 1 wherein said cradle is fixed to said base so as to allow free movement of said cradle relative to said base to operate said translation device, but which prevents said cradle from being lifted off of said base.

7. A computer pointer device as set forth in claim 1 wherein said button comprises two buttons.

8. A new computer pointer control device as set forth in claim 1 wherein said control signals are pointer control signals for moving a computer cursor on a computer screen.

9. A computer pointer control device as set forth in claim 8 wherein said top surface of said base forms a generally partially cylindrical shape having an arc of between 10° and 180°.

10. A computer pointer control device as set forth in claim 9 wherein said top surface of said base forms a generally partially cylindrical shape having an arc of between 30° and 120°.

11. A computer pointer control device as set forth in claim 8 wherein said top surface of said cradle is sized and shaped to accept a human forearm.

12. A computer pointer control device as set forth in claim 8 wherein said top surface of said cradle is sized and shaped to accept a human foot.

13. A computer pointer control device as set forth in claim 1 wherein said translation device is a track ball and said circuit for converting said detected movement into control signals converts rotation of said trackball into said control signals.

14. A computer pointer control device as set forth in claim 1 wherein movement of said cradle along a longitudinal axis of said top surface is converted into control signals corresponding to a first direction and rotation of said cradle about said longitudinal axis is converted into control signals corresponding to a second direction orthogonal to said first direction.

* * * * *